(12) United States Patent
Loeffler et al.

(10) Patent No.: US 10,751,518 B1
(45) Date of Patent: Aug. 25, 2020

(54) SYSTEM AND METHOD FOR DETECTING CEREBROSPINAL FLUID (CSF) FLOW IN AN IMPLANTED SHUNT

(71) Applicants: Cullen Loeffler, Austin, TX (US); Dhruvish Shah, Austin, TX (US)

(72) Inventors: Cullen Loeffler, Austin, TX (US); Dhruvish Shah, Austin, TX (US)

( * ) Notice: Subject to any disclaimer, the term of this patent is extended or adjusted under 35 U.S.C. 154(b) by 0 days.

(21) Appl. No.: 16/693,530

(22) Filed: Nov. 25, 2019

(51) Int. Cl.
*A61M 27/00* (2006.01)

(52) U.S. Cl.
CPC ... *A61M 27/006* (2013.01); *A61M 2205/3334* (2013.01); *A61M 2205/3523* (2013.01); *A61M 2205/3569* (2013.01); *A61M 2205/502* (2013.01)

(58) Field of Classification Search
None
See application file for complete search history.

(56) References Cited

U.S. PATENT DOCUMENTS

| | | | |
|---|---|---|---|
| 2011/0205083 A1* | 8/2011 | Janna | H01Q 7/02 340/870.31 |
| 2015/0094644 A1* | 4/2015 | Lenihan | A61M 27/006 604/9 |
| 2016/0045654 A1* | 2/2016 | Connor | A61M 1/125 600/17 |

* cited by examiner

*Primary Examiner* — Thomas S McCormack
(74) *Attorney, Agent, or Firm* — Dale J. Ream

(57) ABSTRACT

The present invention provides sensor systems and methods of using the same. The sensor systems include implantable sensors and readers configured to communicate with the implantable sensors. The implantable sensors are attachable to catheters and work with the readers to determine the presence of fluid flow and to calculate an absolute measure of fluid flow rate within a catheter. The sensor systems are capable of monitoring the flow of CSF fluid within shunt catheters, such as hydrocephalus shunt catheters.

18 Claims, 6 Drawing Sheets

SYSTEM AND METHOD FOR DETECTING CEREBROSPINAL FLUID (CSF) FLOW IN AN IMPLANTED SHUNT

REFERENCE TO RELATED APPLICATIONS

This application is related to provisional patent application Ser. No. 62/697,734, filed Jul. 13, 2018, and entitled Internal Flow Detection and Measurement in Cerebrospinal Fluid Shunts.

BACKGROUND OF THE INVENTION

Hydrocephalus is a relatively common condition where cerebrospinal fluid (CSF) accumulates in the brain causing increased intracranial pressure, brain damage, and death if not treated. In the United States, hydrocephalus affects over 1,000,000 people. The standard treatment is surgery to implant a device called a shunt which is then required for the life of the patient. The shunts fail at a very high frequency (50% within 2 years, 98% within 10 years).

However, the symptoms of shunt failure are nonspecific such as headache, nausea, vomiting, and lethargy. Shunt failure is life-threatening and typically requires urgent surgery for repair or replacement. Therefore, when someone with a shunt experiences a headache or other symptoms, they are admitted to the emergency department of a hospital for testing, including CT or MRI scans. These indirect tests are adequate for detecting shunt malfunction. However, our primary research indicates that 80% of patients undergoing diagnostic tests for shunt malfunction actually have a working shunt and, thus, the symptoms were a "false alarm."

Diagnostic testing like CT and MRI are effective to diagnose the malfunction of the shunt; however, currently there isn't a method to diagnose malfunction without these costly work-ups. A device called ShuntCheck III has tried to solve this problem by cooling an area of skin above the catheter of the shunt and measuring changes in temperature downstream. However, this method is not very sensitive and is user-dependent, resulting in inaccurate results. Other technologies like micro-electric-manufacturing-systems (MEMS) or ultrasound has been proven to be limited in its capability to detect low CSF flow over time.

Therefore, it would be desirable to have a system and method for detecting if an implanted shunt is malfunctioning to properly drain cerebrospinal fluid. Further, it would be desirable to have a system and method for detecting if an implanted shunt is malfunctioning that is non-invasive and does not require costly MRI or CT test. In addition, it would be desirable to have a system and method for detecting if an implanted shunt is malfunctioning that proactively determines if fluid is flowing through the catheter in communication with the implanted shunt. In addition, it will be desirable to measure the flow of the CSF in the shunts to characterize production and flow of the CSF.

SUMMARY OF THE INVENTION

In one aspect, the present invention comprises of two distinct devices, namely an implanted sensor and an external reader. The implanted sensor may include: an encased flow sensing detection element in-line with the shunt, a processor of sensing data, a transceiver, and a power supply.

In one embodiment, the implanted flow sensing detection element includes integrated circuits with at least one sensor, a signal conditioner, and an analog-to-digital converter. In one embodiment the flow sensing element includes an ability to self-trigger the sensing of flow of fluid. In one embodiment the sensing element includes at least one temperature sensor. In another embodiment the sensing element includes at least one pressure sensor.

In another embodiment, the implanted sensor can be controlled by an external reader to manage power, and configure sensing parameters.

In one embodiment the external reader consists of a transceiver, a processor, and user input/output interface or combination of thereof. In this embodiment, the external reader communicates with the implanted sensor and receives information from it. Further, the external reader can be capable of triggering the flow measurement in implanted sensor, configuring the implanted sensor, and managing its power state. Further, the reader can be capable of providing CSF flow information on a user interface, i.e. a digital display, continuously or on demand. Further, the reader can be capable of storing the CSF information on the reader memory and display historical data on-demand. The internal reader can be further capable of communicating with the implanted sensor wirelessly.

In one aspect, the invention measures the flow of CSF fluid in the shunt catheter by implanting the implantable sensor in-line with the catheter. The sensing element of the implanted sensor is an integrated circuit consisting of a flow sensor, signal conditioning, and digital calibration on a small integrated circuit. In addition, the implanted sensor consists of a microcontroller which configures the flow sensor integrated circuit and receives data from it via a digital interface. The microcontroller may communicate to the external reader via a Bluetooth, NFC or WiFi interface. The implanted sensor may be controlled by the external reader via Bluetooth protocol, NFC, or WiFi protocol. Furthermore, the implanted sensor may include a power module with a battery to supply power to the flow sensor and the microcontroller, or receive power from the external reader.

In one embodiment, the external reader may be a smart phone or other smart device, which communicates with the microcontroller of the implanted sensor, configures, retrieves data from it, and manages the power state of it. In another embodiment, the external reader provides power remotely to the implanted sensor. Furthermore, in each embodiment the external reader provides a user interface, such as a display screen, to the end-user via a software application where the user can view the flow of CSF inside the implanted sensor. Furthermore, the end-user can also configure, manage power, and view historic data on demand.

BRIEF DESCRIPTION OF THE DRAWINGS

The following detailed description of embodiments of the invention will be better understood when read in conjunction with the appended drawings.

DETAILED DESCRIPTION OF THE PREFERRED EMBODIMENT

The present invention provides sensor systems and methods of using the same. The sensor systems include implantable sensors and corresponding readers configured to power and communicate with the implantable sensors. The implantable sensors may be attachable to catheters and work with the readers to determine the presence of fluid flow and to calculate an absolute measure of a fluid flow rate within a catheter. In a preferred embodiment, the sensor systems are capable of monitoring the flow of cerebrospinal fluid (CSF) within shunt catheters, such as hydrocephalus shunt catheters.

Shunt Flow Sensor System

In one aspect, the present invention provides a sensor system for monitoring fluid flow within a shunt. The sensor system 10 is capable of noninvasively taking an absolute measure of flow speed within a shunt catheter 28, and allows for stable performance during long-term implantation.

Figure 1:
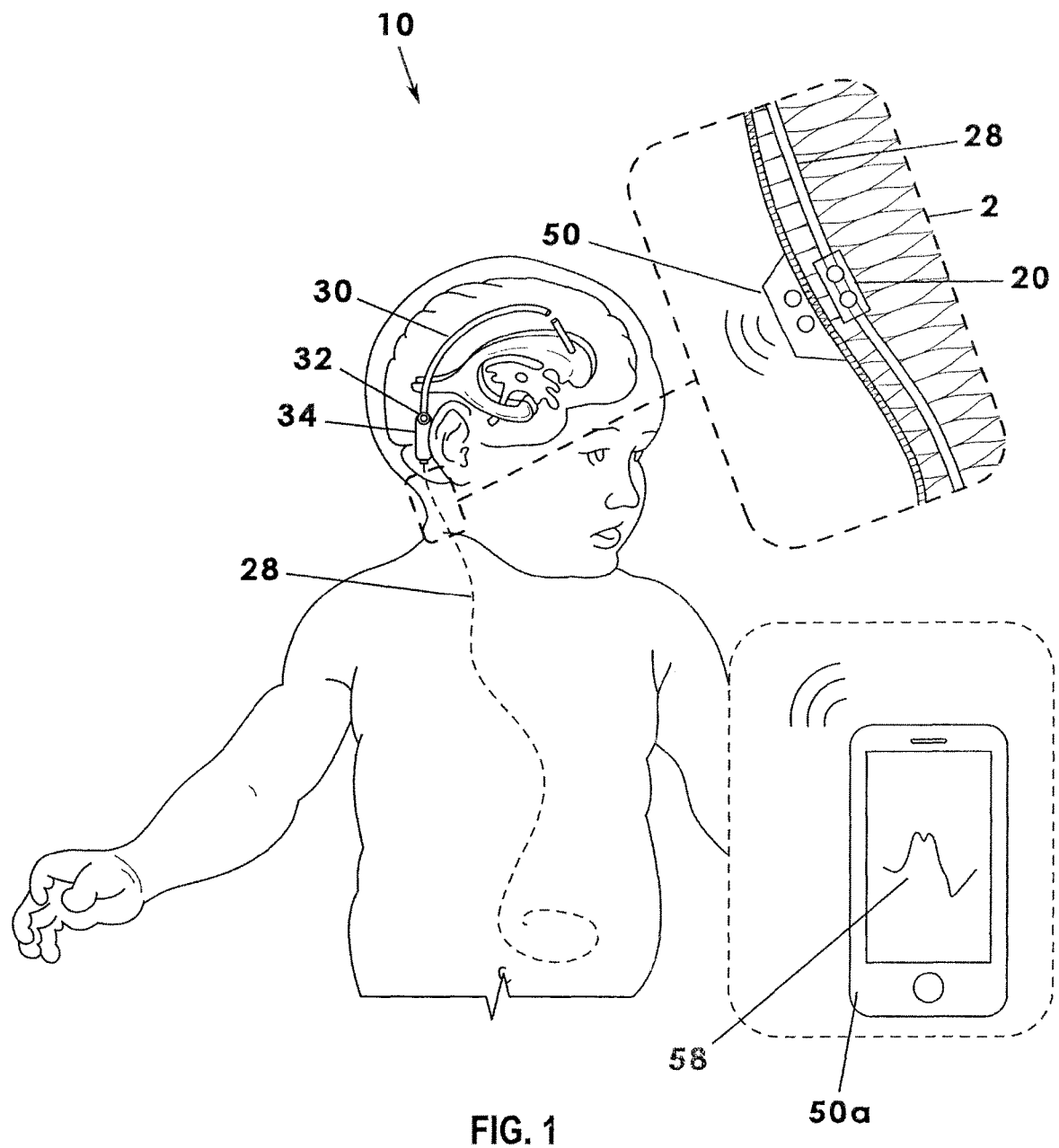
FIG. 1 is a schematic view of a sensory system according to a preferred embodiment of the present invention, such as a sensor implanted with a shunt and catheter in the brain of a patient.

Referring now to FIG. 1, an exemplary sensor system 10 according to the present invention is depicted. The sensor system 10 includes at least one implantable flow sensing assembly 20 and an external reader 50 configured to wirelessly communicate with the implantable flow sensing assembly 20. It is understood that many of the drawings show the implantable sensor assembly 20 already implanted in a patient; nevertheless, the flow sensing assembly will be referred to the "implantable (rather than "implanted") flow sensing assembly" for consistency and clarity. The implantable flow sensing assembly 20 includes a casing 22 that houses several internal components, including at least one sensor 24, a signal conditioner 25, and an analog-to-digital converter 25a. The sensing assembly 20 may, in some embodiments, include its own battery 21 with a boost circuit 21a although, in another embodiment, is configured to draw power from the reader 50. The housing 22 may be constructed from any suitable material, including but not limited to, biocompatible and inert polymers and the like. It is understood that the housing 22 and the electronic components housed therein may be safely implanted in a patient's body.

In the now preferred embodiment, the at least one sensor 24 is a fluid flow sensor. It is understood that fluid flow sensors are used for and capable of gauging mass flow, flow velocity, or a volumetric flow rate of a liquid. In other words, liquid flow can be gauged in a number of different ways, including volumetric or mass flow rates such as liters per second. The fluid flow sensor 24 may include static electronics and be mounted, as in the present case, on a circuit board 27 mounted in the housing 22. Several types of flow sensors may be used in the present application. More particularly, the flow sensor 24 may be a traditional or "off-the-shelf" liquid flow sensing integrated circuit, a custom flow sensing integrated circuit (such as may be designed by an electrical engineer or electronics technician), a low-power flow sensing integrated circuit, and a self-triggering flow sensing circuit. It is understood that the sensing integrated circuit may employ temperature and/or pressure sensing methods. It is also understood that the self-triggering flow sensing circuit refers to a fluid flow sensor that is configured to actuate itself to generate fluid flow data as the flow is detected or at a pre-determined time interval and does not need to be actuated by the reader 50 to do so.

In another embodiment (to be described later), the flow sensor is built with discrete components, such as discrete heating and sensing elements not assembled into an integrated circuit. As will be seen later, a heating element will also be identified by reference numeral 24 as it, in fact, acts as a fluid flow sensor.

Figure 5:
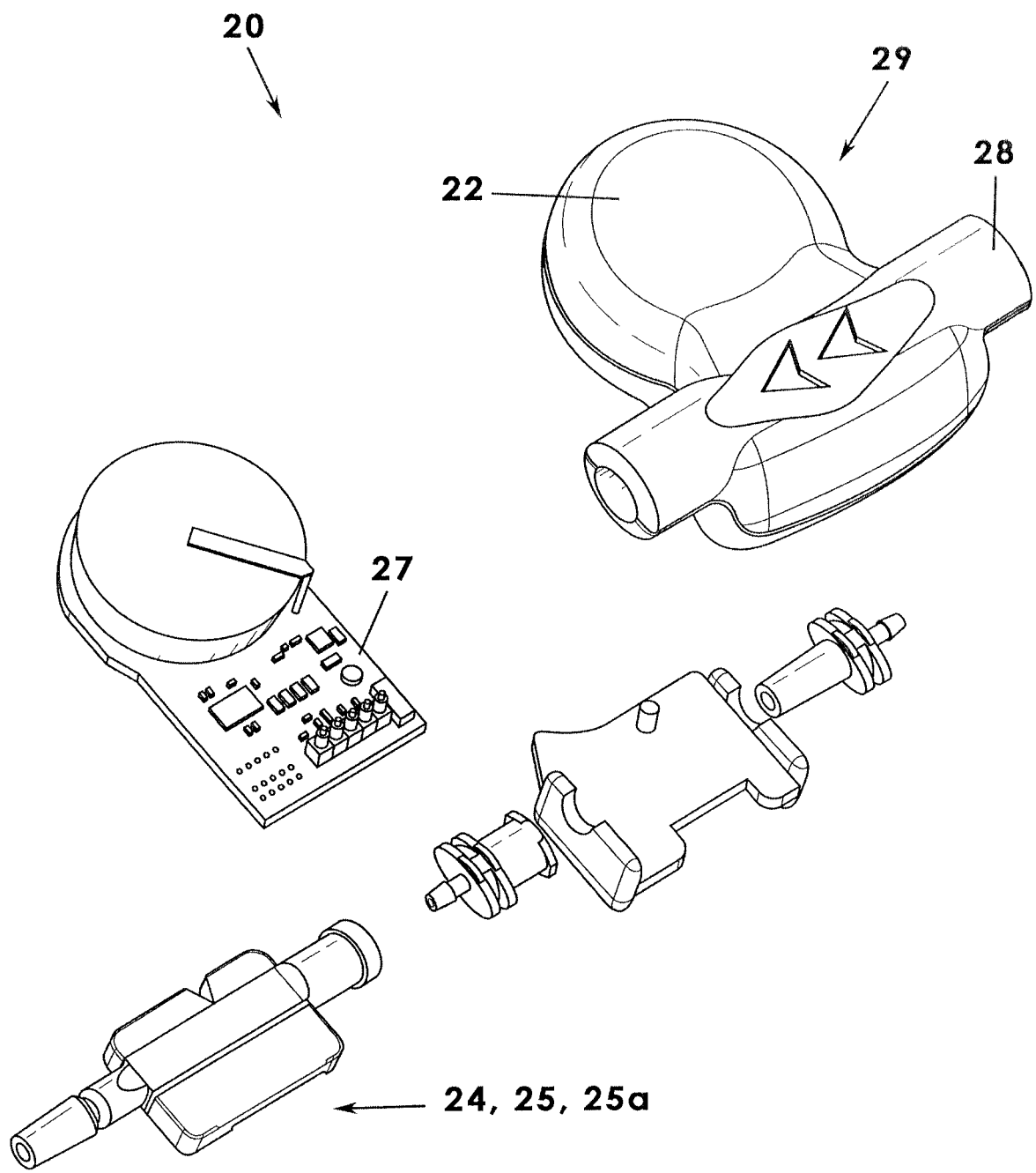
FIG. 5 is an exploded view of an implantable sensor assembly and catheter according to the present invention.

In some embodiments, the implantable flow sensing assembly 20 can be integrated into a catheter 28 as a single unit (referred to herein as an "integrated unit" 29), such as having the casing 22 and catheter 28 (also referred to as a long catheter) that are molded from the same material (FIG. 5). A catheter 28 having an implantable flow sensing assembly 20 can be provided in a shunt system further comprising a short catheter 30 (upstream), a reservoir 32, and a valve 34, as depicted in FIG. 1. In other embodiments, the implantable flow sensing assembly 20 can be provided as a detachable unit, such that the casing 22 may include one or more external fasteners or clips configured to secure the implantable flow sensing assembly 20 to any suitable catheter used in the art.

With further reference to the implantable flow sensing assembly 20, the implantable flow sensing assembly 20 may further include a microcontroller 40 that includes electrical circuitry in communication with the flow sensor 24 for obtaining the fluid flow data and this communication may be implemented using a digital interface 43 as would be known to one of ordinary skill in the electrical and data arts. Further, the microcontroller 40 may further include or be connected to a transmitter 42 for transmitting the fluid flow data. It is understood that the transmitter 42 may be configured as Bluetooth—a technology that allows short distance communication between electronic devices. Alternately, the transmitter 42 may be implemented using Near Field Communications (NFC) technology, Radio Frequency technology, and WiFi. In addition, the microcontroller 40 may include or be connected to a receiver 44 for receiving actuation signals from the reader 50, such as to trigger or actuate the flow sensor 24 to generate fluid flow data indicative of operation of the shunt.

Figures 3, 4:
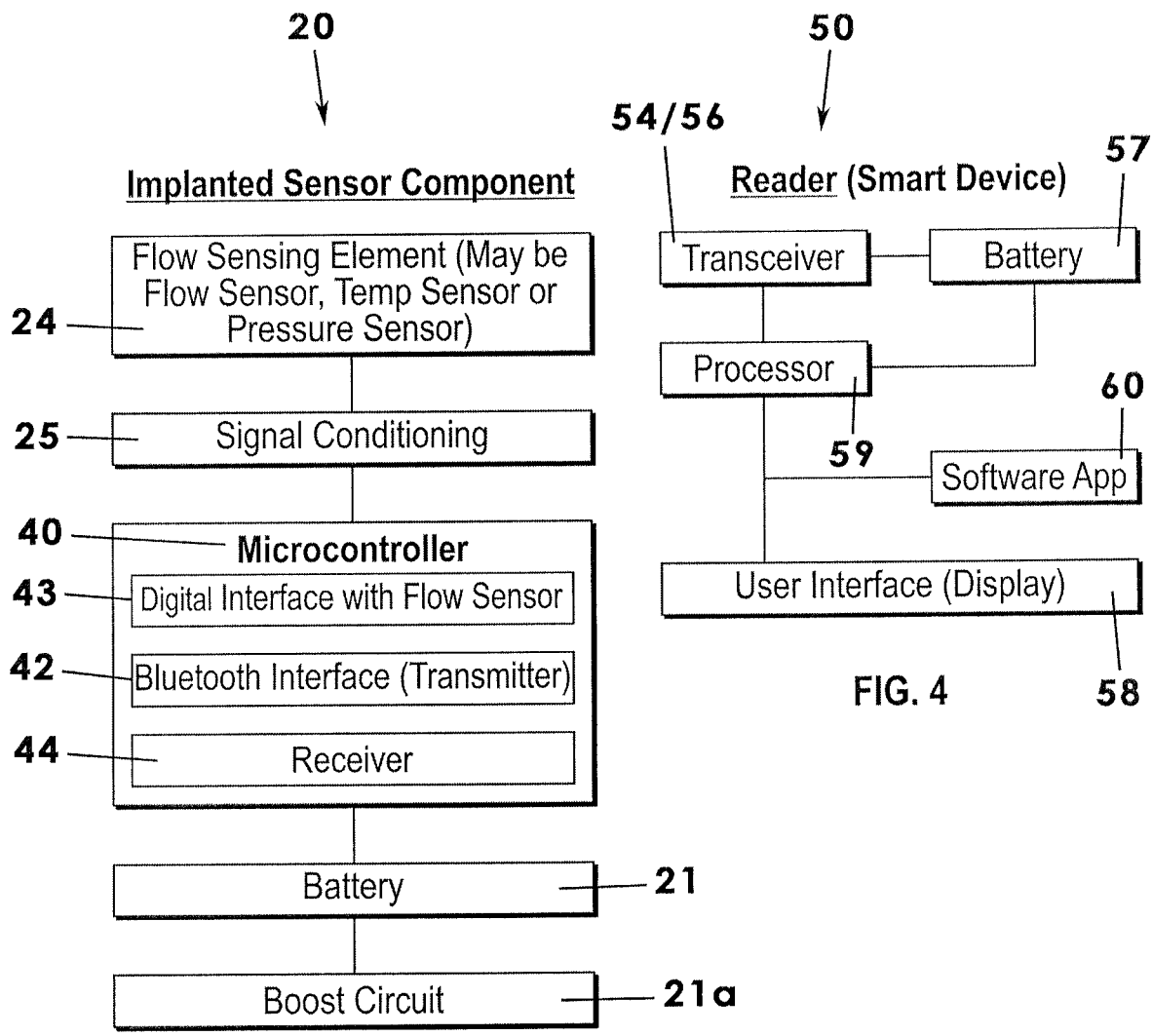
FIG. 3 is a block diagram including electronic elements of an implanted sensor according to the present invention.
FIG. 4 is a block diagram of the electronic elements of a reader component according to the present invention.

In one embodiment, the reader 50 includes a housing 52 encasing a number of internal components, including one or more transmitters 54 and receivers 56 or a combination thereof, i.e. a transceiver 54/56 (FIG. 4). Housing 52 can be constructed from any suitable material, including plastics, polymers, glass, and metals. The one or more transmitters 54 can include radio frequency transmitters configured to transmit a radio signal, such as a signal indicating fluid flow rate data receivable by the one or more receivers of the implantable flow sensing assembly 20. The one or more transmitters 54 can also include inductive coils configured to generate a magnetic field for wireless power generation. The one or more receivers 56 can include radio frequency receivers configured to receive a radio signal, such as a signal indicating a fluid flow reading sent by the one or more transmitters 42 of the implantable flow sensing assembly 20.

Figure 7:
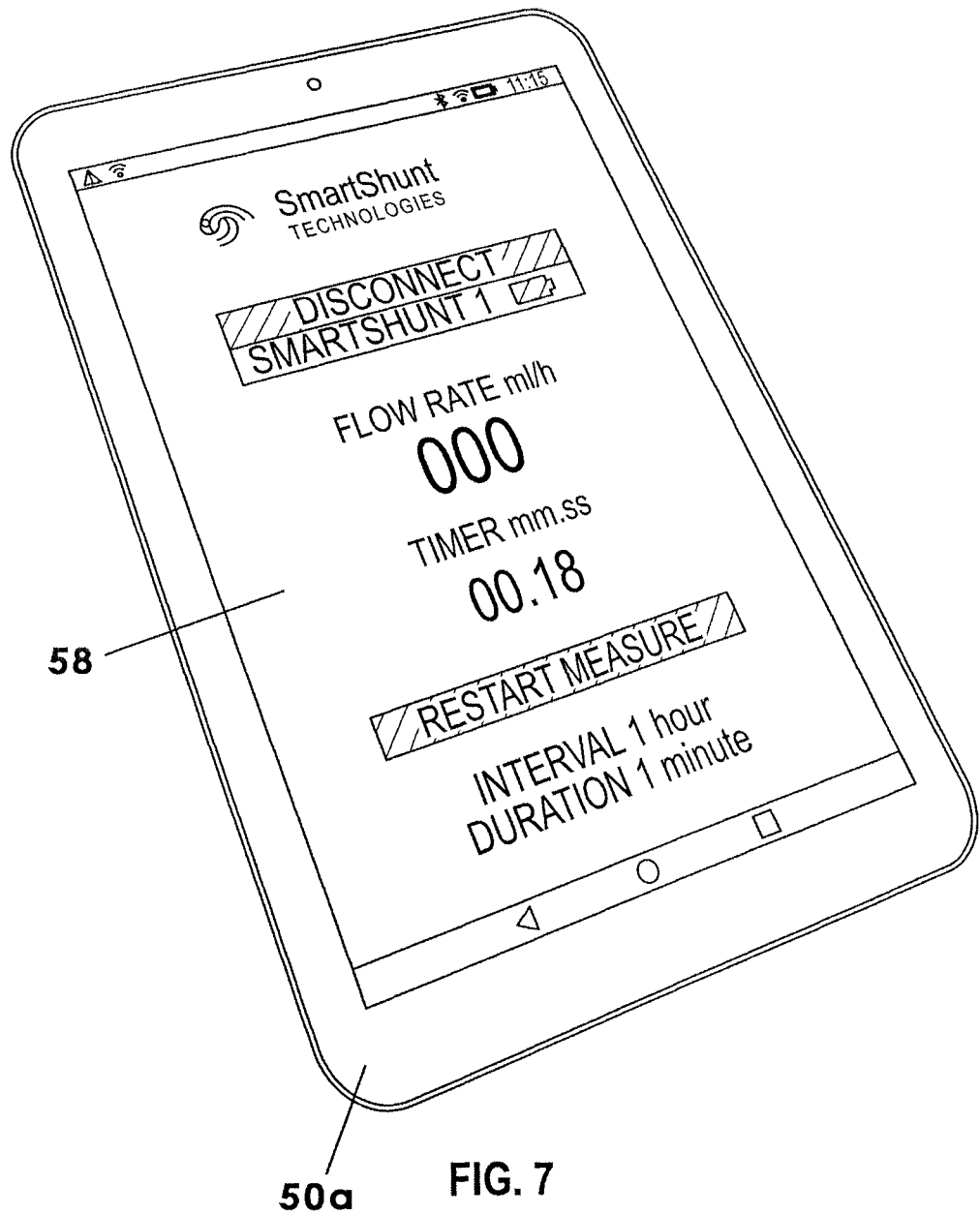
FIG. 7 is a perspective view of one embodiment of the reader according to the present invention.

In some embodiments, reader 50 can be a standalone device referred to by reference character 50a (i.e. single purpose device) having a power supply, such as battery 57, configured to power its various components (FIG. 7). The standalone reader 50 can include a controller for controlling the transmission of signals, a processor for interpreting received signals, and a digital display 58 (also referred to as a user interface) for showing the interpreted signals. The display 58 may be configured to display text and data in multiple formats as are known in the art.

In other embodiments, the reader 50 may operate in conjunction with a computing device including, but not limited to, desktop or mobile devices, laptops, desktops, tablets, smart phones or other wireless digital/cellular phones, televisions or other thin client devices as would be understood by those skilled in the art. The reader 50 may rely on an inbuilt power supply or be powered by the computing device and may rely on the computing device to provide a controller, a processor, and a digital display.

In another aspect, the present invention provides methods for using the sensor systems 10 for monitoring shunt performance. One such method may include a software application 60 running on the computing device or standalone reader 50, the software application including programming configured to be executed by the processor 59 and to interpret fluid flow data received from the implantable flow sensing assembly 20 as described above. Programming and data may be stored in a non-volatile memory (not shown) in communication with the processor 59, as is known in the art. As described elsewhere herein, the sensor systems of the present invention are useful in noninvasively detecting flow in an implanted shunt and are capable of directly measuring the flow rate of fluid within the shunt.

Figure 6:
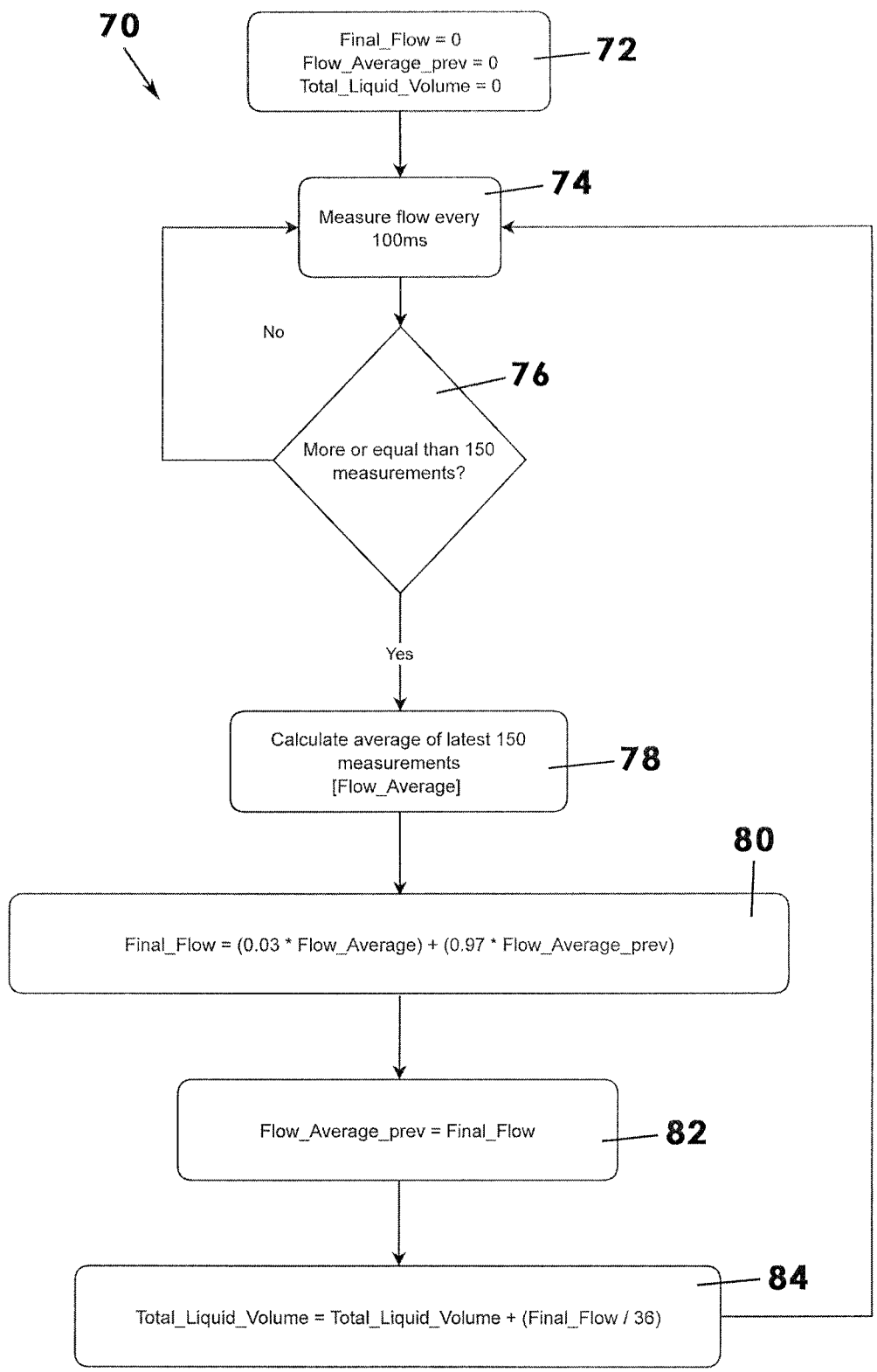
FIG. 6 is a flowchart illustrating the steps of the software application executed by the reader according to the present invention.

More particularly, a process 70 implemented by the processor 59 of the reader 50 is illustrated in FIG. 6 and described below. It is understood that the processor 59 may accomplish the process 70 by execution of the software application (i.e. program steps or circuitry). At step 72, the processor 59 sets certain parameters at predetermined null values. Specifically, a final flow parameter, a previous flow average parameter, and a total liquid volume parameter are set to zero. It is understood that these parameters are initially set to zero to begin the process 70 but will be changed or recalculated repeatedly as the process 70 is executed as will be described below.

At step 74, the processor 59 causes measurements of fluid flow to be actuated at a predetermined rate, such as every 100 microseconds (ms). Specifically, it is understood that the processor 59 may cause the transceiver 54/56 to send an actuation signal to the implantable flow sensor assembly 20 to cause the flow sensor 24 to generate fluid flow data as described above. In other words, the flow sensor 24 operates to detect if fluid is flowing through the adjacent catheter. Fluid flow data is transmitted back to the reader 50 as described above. The process 70 proceeds to step 76.

At step 76, the processor 59 determines if a minimum number of measurements have been taken, for example, if 150 measurements have been taken by the flow sensor 24. If so, the process 70 proceeds to step 78 but, if not, the process 70 loops back to step 74 where another measurement may be taken. At step 78, the processor 59 is configured or programmed to determine and calculate a flow average of the predetermined number of flow measurements (e.g. an average of 150 measurements). The calculated flow average is assigned to a parameter representing a flow average. The process 70 proceeds to step 80.

At step 80, the processor 59 is caused to make another calculation, namely, the process 70 determines that a Final Flow is equal to the sum of two products as represented below:

$$Final\_Flow = (0.03 * Flow\_Average) + (0.97 * Flow\_Average\_Prev)$$

Expressed in words, the final flow is equal to 3% of the calculated flow average plus 97% of the previous flow average. The process 70 proceeds to step 82 at which the previous average flow parameter is set equal to the recently calculated Final Flow parameter. The process 70 proceeds to step 84 at which a total liquid volume is calculated based on the received fluid flow data. Specifically, the total liquid volume is calculated according to the following calculation:

$$Total\_Liquid\_Volume = Total\_Liquid\_Volume + (Final\_Flow/36)$$

To be clear, the total fluid passing through the catheter 28 is measured by the sensory system 10 in data communication with the reader 50.

Finally, the software application 60, which is in communication with the processor 59 and user interface 58, is configured to publish a "No Fluid Flow" or similar message on the user interface (i.e. display screen) if the fluid flow data is indicative of fluid not flowing through the catheter 28. Specifically, the message indicating an insufficient fluid flow may be a result of the Final Flow being less that a predetermined quantity.

Figure 2:
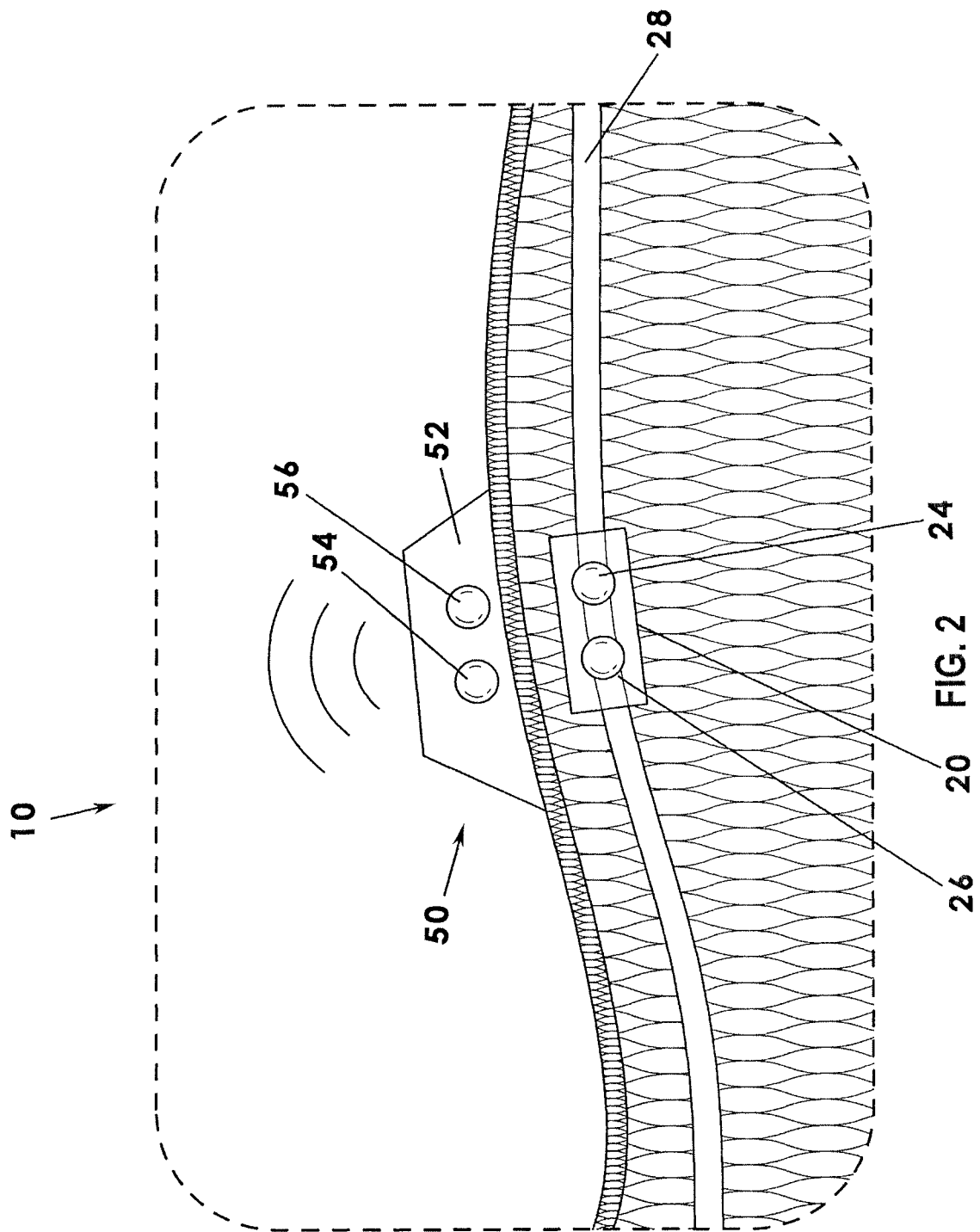
FIG. 2 is an isolated view on an enlarged scale taken from FIG. 1.

As described above, the sensor systems of the present invention 25 include at least one implantable flow sensing assembly 20 attachable to a catheter 28 and an external reader 50. Reader 50 can be positioned adjacent to the implantable flow sensing assembly 20, such as by resting on the skin of a patient or by holding the reader 50 near the site of implanted sensor (FIGS. 1 and 2). The reader 50 is configured to provide power to the at least one transmitter of implantable flow sensing assembly 20 based on the proximity between reader 50 and the implantable flow sensing assembly 20, wherein the proximity can be as close as a few millimeters and as far as a few feet.

It is also contemplated that fluid flow through a catheter may also be determined using flow sensors constructed using discrete components other than the integrated fluid flow sensor 24 described above and such sensors, specifically a heating element and a corresponding temperature sensor will be described below.

The heating element is a sensor and is also referred to by reference numeral 24. Heating element 24 and the at least one temperature sensor 26 are arranged within housing 22 such that they are positioned adjacent to catheter 28, or in the case of a detachable sensor 20, such that they are positioned adjacent to a catheter 28 when sensor 20 is attached to catheter 28. Heating element 24 can be any suitable heating element, including but not limited to a thermoelectric heater, a Peltier heater, an infrared heater, and the like. The at least one temperature sensor 26 may include any suitable temperature sensing element, including but not limited to thermocouples, thermistors, and the like. In certain embodiments, heating element 24 and the at least one temperature sensor 26 are in linear alignment relative to a catheter 28, such that in a catheter 28 having a downstream flow from a first end to a second end, heating element 24 is positioned upstream from the at least one temperature sensor 26. In one embodiment, a first temperature sensor 26 is positioned downstream from heating element 24, and the second temperature sensor 26 may be positioned downstream from the heating element 24 by a distance of between about 1 to 5 mm, wherein heating element 24 and the first temperature sensor 26 are in linear alignment.

In various embodiments, the implantable sensing assembly 20 further includes one or more receivers, transmitters, and capacitors. The one or more receivers can include radio frequency receivers configured to receive a radio signal, such as a signal indicating a temperature setting for heating element 24. The one or more receivers can also include inductive coils configured to respond to a magnetic field for wireless power generation. The one or more capacitors can be electrically connected to the inductive coils to store wirelessly generated electricity power. The one or more capacitors can also be electrically connected to heating element 24 for heat generation. The one or more transmitters can include radio frequency transmitters that are electrically connected to the at least one temperature sensor 26 and configured to transmit a radio signal, such as a signal indicating a temperature reading.

In some embodiments, heating element 24 is configured to increase the temperature of an adjacent flow of fluid above an ambient temperature, or above a typical body temperature between about 34° C. and 38° C. Sensor system is thereby capable of detecting the existence of a fluid flow based on the temperature measured by the at least one temperature sensor 26 downstream of heating element 24. For example, in a scenario where the at least one temperature sensor 26 measures a series of temperatures that is unchanged as heating element 24 applies heat, or after heating element 24 has ceased applying heat, reader 50 may indicate that there is no fluid flow in a catheter. In a scenario where the at least one temperature sensor 26 measures a series of temperatures that increase as heating element 24 applies heat and decrease after heating element 24 has ceased applying heat, reader 50 may indicate that there is a flow of fluid in a catheter.

Sensor system 10 is also capable of providing an absolute measure of a fluid flow within a catheter. The flow of fluid can be based on a thermal time-of-flight calculation. For example, in a scenario where heating element 24 has increased the heat of a flow of fluid to a set temperature, at least one temperature sensor 26 can measure the instant temperature of the fluid downstream of heating element 24. In some embodiments, the flow rate of the fluid can be calculated based on the difference between the set temperature of heating element 24 and the measured temperature or temperatures at the at least one temperature sensor 26. In other embodiments, the flow rate of the fluid can be calculated based on the difference between the measured temperature or temperatures at a first temperature sensor 26 and at least a second temperature sensor 26 downstream from the first temperature sensor. In various embodiments, the sensor system is configured to detect flow rates of about 0.3 mL/min, or to detect linear flow rates of between about 0.5 to about 1.0 mm/sec.

Reader 50 is also configured to provide a signal that activates the heating element 24 of the implantable sensing assembly 20, which increases the temperature of a flow of fluid passing through the catheter 28. The at least one temperature sensor 26 downstream of heating element 24 measures the temperature of the same flow of fluid as it passes by, and the implantable sensing assembly 20 is configured to transmit the temperature readings via its at least one transmitter to the at least one receiver 56 of reader 50.

In some embodiments, the implantable sensing assembly 20 having capacitors has sufficient residual power to perform the transmission of temperature readings, permitting reader 50 to be moved away from the implantable sensing assembly 20. Reader 50 is configured to interpret the received temperature readings as a determination of whether a fluid flow is present in the 10 catheter, and calculate an absolute measure of the flow rate.

The disclosures of each and every patent, patent application, and publication cited herein are hereby incorporated herein by reference in their entirety. While this invention has been disclosed with reference to specific embodiments, it is apparent that other embodiments and variations of this invention may be devised by 10 others skilled in the art without departing from the true spirit and scope of the invention. The appended claims are intended to be construed to include all such embodiments and equivalent variations.

What is claimed is:

1. A flow sensor system for determining if fluid is flowing through a shunt catheter implanted in a patient in need of an implanted shunt, said flow sensor system, comprising:
    an implantable flow sensing assembly attached to the shunt catheter and including a casing that defines an interior area;
    wherein said implantable flow sensing assembly includes a flow sensor positioned in said interior area of said casing and that, when actuated, is configured to generate fluid flow data indicative of the fluid flowing through the shunt catheter;
    wherein said implantable flow sensing assembly includes a transmitter configured to transmit said generated fluid flow data;
    a reader having a housing defining an interior space, wherein said reader includes a processor positioned in said interior space and in electrical communication with a power source,
    said reader including a transceiver configured to actuate said flow sensor to generate fluid flow data when said housing is placed in close proximity to the implantable flow sensing assembly and to receive said transmitted fluid flow data;
    wherein said reader includes a software application in data communication with said processor that causes the processor to:
        actuate said flow sensor to generate said fluid flow data at a predetermined rate until a predetermined number of measurements have been made;
        determine a current flow average using said predetermined number of measurements;
        determine a final flow by summing (1) the product of the current flow average and a first predetermined constant and (2) the product of a previous flow average and a second constant; and
        set said previous flow average to be equal to said current flow average.

2. The sensor system of claim 1, wherein said implantable flow sensing assembly includes a microcontroller in communication with said flow sensor, said microcontroller including said transmitter configured to transmit said fluid flow data and including a receiver configured to receive an actuation signal from said reader.

3. The sensor system of claim 1, wherein the implantable flow sensing assembly is implanted in-line with the shunt catheter.

4. The sensory system of claim 1, wherein said flow sensor is selected from the group consisting of a liquid flow sensing integrated circuit, a custom flow sensing integrated circuit, a low-power flow sensing integrated circuit, and a self-triggering flow sensing circuit.

5. The sensory system as in claim 4, wherein said transmitter of said implantable flow sensing assembly and said transceiver of said reader are configured to communicate using one of radio frequency (RF), WiFi, or Near Field Communication (NFC) signal protocols.

6. The sensory system as in claim 1, wherein the reader includes a user interface in data communication with said processor for displaying said fluid flow data received by said transceiver.

7. The sensory system as in claim 6, wherein said user interface is a display screen.

8. The sensory system as in claim 1, wherein said reader is one of a smart phone or a smart device.

9. The sensory system of claim 1, wherein said software application causes said processor to determine a new total liquid volume by summing a current total liquid volume and a quotient of the final flow divided by 36.

10. A method for determining if fluid is flowing through a shunt catheter implanted in a patient in need of an implanted shunt, said method, comprising:
   attaching an implantable flow sensing assembly the shunt catheter, said implantable flow sensing assembly including a casing that defines an interior area;
   positioning a flow sensor in said interior area of said casing of said implantable flow sensing assembly and configuring said flow sensor so that, when actuated, said flow sensor generates fluid flow data indicative of fluid flowing through the shunt catheter;
   transmitting said generated fluid flow data via a transmitter associated with said implantable flow sensing assembly;
   receiving said transmitted fluid flow data via a transceiver of a reader when said reader is positioned in close proximity to said implantable flow sensing assembly;
   displaying said received fluid flow data on a user interface of said reader;
   wherein said reader includes:
      a housing defining an interior space and having a processor positioned in said interior space and in electrical communication with a power source;
      a software application in data communication with said processor and configured to cause said processor to:
         actuate said flow sensor to generate said fluid flow data at a predetermined rate until a predetermined number of measurements have been made;
         determine a current flow average using said predetermined number of measurements;
         determine a final flow by summing (1) the product of the current flow average and a first predetermined constant and (2) the product of a previous flow average and a second constant; and
         set said previous flow average to be equal to said current flow average.

11. The method of claim 10, wherein said implantable flow sensing assembly includes a microcontroller in communication with said flow sensor, said microcontroller including said transmitter configured to transmit said fluid flow data and including a receiver configured to receive an actuation signal from said reader.

12. The method of claim 10, wherein the implantable flow sensing assembly is implanted in-line with the shunt catheter.

13. The method as in claim 10, wherein the reader includes a user interface in data communication with said processor for displaying said fluid flow data received by said transceiver.

14. The method as in claim 13, wherein said user interface is a display screen.

15. The method as in claim 10, wherein said reader is one of a smart phone or a smart device.

16. The method of claim 10, further comprising:
   said reader actuating said flow sensor to generate said fluid flow data at a predetermined rate until a predetermined number of measurements have been made;
   said reader determining a current flow average using said predetermined number of measurements;
   said reader determining a final flow by summing (1) the product of the current flow average and a first predetermined constant and (2) the product of a previous flow average and a second constant; and
   said reader setting said previous flow average to be equal to said current flow average.

17. The method of claim 1, wherein said software application causes said processor to determine a new total liquid volume by summing a current total liquid volume and a quotient of the final flow divided by 36.

18. The method of claim 17, further comprising said processor displaying a no-flow message on said user interface if said total flow is less than a predetermined parameter.

* * * * *